United States Patent

Nakatsuyama et al.

[11] Patent Number: 5,116,941
[45] Date of Patent: May 26, 1992

[54] PEPTIDE SUBSTRATES FOR DETERMINATION OF ENZYME ACTIVITY

[75] Inventors: Shuichi Nakatsuyama; Yoshio Nakamura; Katsumasa Kuroiwa, all of Koriyama; Takeshi Nagasawa, Urawa, all of Japan

[73] Assignee: Nitto Boseki Co., Ltd., Fukushima, Japan

[21] Appl. No.: 378,850

[22] Filed: Jul. 12, 1989

[30] Foreign Application Priority Data

Jul. 14, 1988 [JP] Japan .................. 63-173789

[51] Int. Cl.$^5$ .............. C07K 5/06; C07K 5/08; C07K 5/10
[52] U.S. Cl. .................. 530/331; 530/330; 546/208; 546/223
[58] Field of Search .............. 546/223, 208; 530/331, 530/330

[56] References Cited

U.S. PATENT DOCUMENTS

| | | | |
|---|---|---|---|
| 3,821,188 | 6/1974 | McKinley et al. | 530/331 |
| 3,966,700 | 6/1976 | Mattalia | 530/331 |
| 4,386,073 | 5/1983 | Kisfaludy et al. | 530/331 |
| 4,434,096 | 2/1984 | Coleman et al. | 530/331 |
| 4,619,916 | 10/1986 | DiStazio et al. | 530/331 |
| 4,650,753 | 3/1987 | Nagasawa et al. | 530/331 |

Primary Examiner—Lester L. Lee
Attorney, Agent, or Firm—Darby & Darby

[57] ABSTRACT

Compounds represented by the following formula:

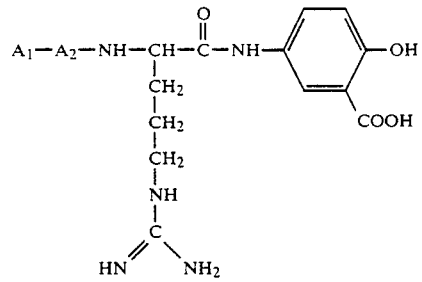

wherein $A_1$ and $A_2$ each represents a specific amino acid residue, are excellent as substrates for determination of enzyme activity such as trypsin, etc.

5 Claims, No Drawings

PEPTIDE SUBSTRATES FOR DETERMINATION OF ENZYME ACTIVITY

BACKGROUND OF THE INVENTION

1. Field of the Invention

The present invention relates to substrates for determination of enzyme activity which are useful for assaying enzyme activity of trypsin or the like. The substrates of the present invention permit to quantitatively determine trypsin with extremely high selectivity as compared to substrates hitherto reported so that the substrates are utilizable to study reactions in which trypsin is produced, inhibited or consumed, and also to assay for factors relating to these reactions, for example, trypsinogen and trypsin inhibitor. The substrates are also useful as diagnostics of pancreatitis in the medical field.

2. Related Art Statement

As a method for determining enzyme activities of trypsin, etc. which comprises reacting enzymes with substrates and colorimetrically measuring the produced color-forming compound, many techniques have been developed so far.

For example, as a substrate for determination of trypsin activity, protein such as gelatin and hemoglobin, etc. had been used from the old. However, it is inappropriate to assay for trypsin activity in the pancreatic juice or duodenal juice using the substrate, since other proteinases, for example, chymotrypsin, etc., are present in such a juice. It was reported by Bergman et al. that trypsin has also the action of amidase and esterase, in addition to its proteolytic activity [J. Biol. Chem., 130, 81–86 (1939)]. Since then, many synthetic substrates, for example, Benzyl-L-Arg-OEt, p-Toluenesulfonyl-L-Arg-p-Nitroanilide, etc. have been developed. However, these substrates encounter problems that substrate specificity is low and sensitivity is low. Furthermore, Benzyloxy-carbonyl-Val-Gly-Arg-p-Nitroanilide (CHR-TRY, Pentapharm Corp., U.S. Pat. No. 4,278,762) has been developed as a substrate for assaying trypsin activity.

In general, it is important that synthetic substrates for determination of enzyme activity have properties such as high sensitivity and high specificity to enzyme, good solubility in water or in buffer and easy detectability of color-forming compounds which are degradation products of the substrates, and the like.

Among them, high specificity to the enzyme to be assayed is particularly important and the best substrate for assaying trypsin activity developed heretofore is CHR-TRY described above. However, even CHR-TRY is not necessarily satisfactory in therms of specificity to enzyme.

That is, it is known that CHR-TRY considerably reacts with proteolytic enzymes such as thrombin, plasmin and factor Xa, other than trypsin.

In addition, a method for assaying trypsin using a substrate such as CHR-TRY involves reacting the substrate with trypsin to produce p-nitroaniline and quantitatively determining the thus produced chromophoric compound. In the case of colorimetrically determining the yellow color of the produced p-nitroaniline, contaminates in a sample collected from the living body unavoidably affect the results.

SUMMARY OF THE INVENTION

An object of the present invention is to provide substrates for determination of enzyme activity which permits to readily assay enzyme such as trypsin, etc., possess high sensitivity and high specificity to enzyme, are excellent in solubility in water or buffer solutions and provide easy detectability of degradation products, etc.

According to the present invention, there are provided substrates for determination of enzyme activity represented by the following general formula:

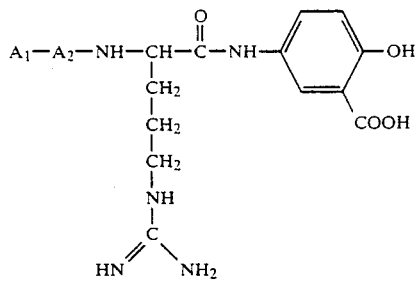

wherein
$A_1$ represents L- or D-PyroGlu or L- or D-Glu(OR) (wherein OR is a group binding to $\gamma$-carboxyl group of glutamic acid; R represents hydrogen or an aliphatic hydrocarbon residue of 1 to 8 carbon atoms); and,
$A_2$ represents Gly, Pro, Pip, Ala, Val, But, NVal or NLeu; and acid addition salts thereof.

The substrates for determination of enzyme activity of the present invention are characterized by having 3-carboxy-4-hydroxyaniline residue as a chromophore. The substrates of the present invention contain hydroxy group and carboxy group in the chromophore which are extremely highly hydrophilic and hence, possess excellent solubility in water.

PREFERRED EMBODIMENTS OF THE INVENTION

Abbreviations as used in the specification are as follows.
Arg: arginine
Gly: glycine
Pro: proline
Pip: pipecolic acid
Ala: alanine
Val: valine
But: 2-aminobutyric acid
NVal: norvaline
NLeu: norleucine
Glu: glutamic acid
PyroGlu: pyroglutamic acid
Arg($NO_2$): arginine, $\delta$-gaunidino group of which is protected with nitro group
Z: benzyloxycarbonyl
BOC: tert-butyloxycarbonyl
Bz: benzyl
Tos: p-toluenesulfonyl
DMF: dimethylformamide
MeOH: methanol
NEM: N-ethylmorpholine
—SPD: 4,6-dimethylpyrimidine-2-thio
—OSu: succinimidoxy
—O$^t$Bu: t-butoxy
O$^n$Pr: n-propyloxy
—O$^i$Pr: i-propyloxy
—PNA: p-nitroanilide —CHA: 3-carboxy-4-hydroxyanilide
TLC: thin layer chromatography
GPC: gel filtration chromatography
AcOH: acetic acid
BuOH: n-butanol
AcOEt: ethyl acetate In formula [I] above, A represents L- or D-PyroGlu or L- or D-Glu(OR), wherein OR is a group binding to γ-carboxyl group of glutamic acid; R represents hydrogen or an aliphatic hydrocarbon residue of 1 to 8 carbon atoms. When R is an aliphatic hydrocarbon group, OR forms an ester group. As such aliphatic hydrocarbon group, there may be exemplified an alkyl of 1 to 8 carbon atoms such as methyl, ethyl, iso-propyl, n-propyl, n-butyl, tert-butyl, pentyl, hexyl, octyl, etc.; a cycloalkyl of 3 to 8 carbon atoms such as cyclobutyl, cyclopentyl, cyclohexyl, cycloheptyl, cyclooctyl, etc. Of these, an alkyl of 1 to 4 carbon atoms such as methyl, ethyl, iso-propyl and n-propyl are preferred.

$A_2$ represents Gly, Pro, Pip, Ala, Val, But, NVal or NLeu.

The amino acid residue in formula [I] above is L-form, unless otherwise indicated.

The present substrates for determination of enzyme activity may be in the form of acid addition salts thereof. As such acid addition salts, there may be exemplified inorganic acid salts such as hydrochlorides, hydrobromides, phosphates, sulfates, nitrates, etc.; organic acid salts such as succinates, citrates, lactates, malates, benzenesulfonates, etc.

The substrate of the present invention represented by formula [I] described above can be synthesized by techniques well known in peptide chemistry.

That is, the substrate of the present invention can be synthesized by firstly binding 3-carboxy-4-hydroxyaniline as a chromophore to arginine and sequentially coupling with amino acids. Alternatively, the substrate of the present invention can also be synthesized by previously synthesizing dipeptide fragment ($A_1$-$A_2$ moiet in formula [I]) and reacting the fragment with arginine to which a chromophore has been bound.

In the above coupling or binding reaction, amino groups and carboxyl groups which are present in the molecules of the amino acids, dipeptide fragment, etc. used for the reaction but do not participate directly in the reaction are protected with protective groups ordinarily used in peptide synthesis.

As the amino protecting group, it is advantageous to use carbobenzoxy or tert-butyloxycarbonyl, or groups associated therewith, for example, p-methoxy, p-nitro or p-methoxyphenylazolecarbobenzoxy, and the like. As the carboxyl protecting group, it is advantageous to use ester groups with benzyl, tert-butyl, etc. in the case of using arginine in the reaction, δ-guanidino present in arginine is protected. For the protection, it is advantageous to use nitro or protonation.

The protective groups described above can be removed or split off in a conventional manner, after the reaction.

Coupling of two amino acids, coupling of dipeptide fragment with amino acid, coupling of 3-carboxy-4-hydroxyaniline with arginine, etc. can be effected by the activated ester method, mixed acid anhydride method or carbodiimide method conventionally used in peptide synthesis.

The activated ester method involves activation of α-carboxyl group. It is advantageous to use, for example, N-hydroxysuccinimide, p-nitrophenol, trichlorophenol, 4,6-dimethylpyrimidyl-2-thiol, etc.

For the mixed acid anhydride method, the use of monoalkyl carbonates chloride, for example, isobutylchloroformate, is advantageous.

In the carbodiimide method, carbodiimides are used; it is beneficial to perform the method in the presence of, for example, N,N'-dicyclohexylcarbodiimide (DCC).

The esterification of the carboxyl at the γ-position of glutamic acid in the Glu(OR) moiety of formula [I] is advantageously performed by condensation with the corresponding alcohol, for example, dehydration condensation with iso-propanol, etc., for example, in the presence of an acid catalyst.

The characteristic feature of the substrate of the present invention for determination of enzyme activity lies particularly in excellent substrate specificity to trypsin. Relative reactivities of the novel substrate of the present invention, for example, PS-1245: H-PyroGlu-Ala-Arg-CHA, and known substrate CHR-TRY (Pentapharm Inc., Comparative Example) with trypsin (Try), thrombin (TH), plasmin (PL), factor Xa (FXa), etc. which are proteases are shown in Table 1, when CHR-TRY is made 100. In the case of the novel substrate of the present invention, reactivities with thrombin, plasmin, factor Xa, etc. are extremely low; the substrate does not react with thrombin only in 12%, with plasmin in 36% and with factor Xa in 19% but shows reactivity with trypsin as extremely high as 278%. Therefore, the results reveal that the novel substrate of the present invention has an excellent substrate specificity particularly to trypsin.

TABLE 1

| Relative Reactivity of Substrate to Each Enzyme | | | | |
|---|---|---|---|---|
| | Try | TH | PL | FXa |
| CHR—TRY (Comparative Example) | 100 | 100 | 100 | 100 |
| Z—Val—Gly—Arg—PNA | (0.243) | (0.050) | (0.014) | (0.090) |
| PS-1245 (substrate of the invention) | 278 | 12 | 36 | 9 |
| H—PyroGlu—Ala—Arg—CHA | (0.676) | (0.006) | (0.005) | (0.008) |

Initial substrate concentration: So = 0.4 mmol

Numerals within parenthesis indicate O.D. values measured.

The substrate of the present invention is used to determine enzyme activity such as trypsin, etc., as described hereinabove. In this case, the substrate is acted on, e.g., trypsin, in a buffer solution with pH between 8.0 and 10.0, the produced 3-carboxy-4-hydroxyaniline is led to a suitable color-forming substance and the color-forming substance is quantitatively determined by colorimetry, whereby, for example, trypsin activity can be determined. Alternatively, it is also possible to determine, e.g., trypsin activity, by fluorometry at an excited wavelength of 328 nm and a fluorescent wavelength of 540 nm.

To lead to a color-forming substance, there are known the pentacyanoamineferroate method and the method for oxidative condensation with coupler. As the coupler, there are used aniline compounds, e.g., N,N-diethylaniline, in the case of forming a color in an acidic region and in the case of forming a color in an alkaline region, phenol, naphthol, 2,6-xylenol, thymol, o-cresol, o-ethylphenol, etc. are used.

As oxidizing agents for the oxidative condensation, there are used various oxidizing agents such as hydrogen peroxide, persulfates, etc. but preferred is metaperiodic acid.

By leading 3-carboxy-4-hydroxyaniline to an appropriate color-forming substance, the maximum absorption wavelength can be distributed in the range of 560 to 770 nm; in this case, temperature-dependent change in color formation is extremely small and the substance is stable and suitable for determination of enzyme activity such as trypsin. Further in terms of color sensitivity, 3-carboxy-4-hydroxyaniline provides an extremely large absorbance. In more detail, in the case of color-forming p-nitroaniline produced from known substrate, $\epsilon$ is 10,600 at ordinary measurement wavelength of 405 nm. Turning to the present invention, $\epsilon$ is 21,500 at $\lambda=700$ nm according to the pentacyanoamineferroate method described above and, in color formation according to the oxidative condensation method, $\epsilon$ is 29,000 at $\lambda=645$ nm in the case of o-ethylphenol and $\epsilon$ is 21,600 at $\lambda=615$ nm in the case of 2,6-xylenol. Also from this aspect, the substrate of the present invention is extremely advantageous in quantitative assay.

One of the characteristic features of the present invention is that the substrate is hardly affected by impurities or contaminates in a sample collected from the living body. This is because measurement is made at wavelengths longer than 560 nm when using the substrate of the present invention, whereas in the case of p-nitroanilide compound known to be substrates, measurement is made at wavelengths shorter than 560 nm. Therefore, the substrate is little affected by the impurities in a sample. This characteristic feature coupled with high specificity inherent to the substrate of the present invention results in accurate measurement.

As stated above, it is clear that the substrate of the present invention is extremely superb for determination of enzyme activity such as trypsin or the like, as compared to conventional substrates. The substrate of the present invention is extremely useful as diagnostic of Pancreatitis.

The present invention is described in more detail by referring to the examples below but is not deemed to be limited to these examples.

In the examples below, amino acids are all L-form, unless otherwise indicated.

In thin layer chromatography (TLC), silica gel $F_{254}$ (manufactured by Merck) plate was used. As solvents, those having the following compositions were used.

$R_{f1}$ CHCl$_3$:MeOH:AcOH:H$_2$O = 80:20:5:2.5
$R_{f2}$ n-BuOH:AcOH:H$_2$O = 4:1:1
$R_{f3}$ n-BuOH:AcOH:H$_2$O = 4:1:2
$R_{f4}$ n-BuOH:AcOH:H$_2$O = 4:1:5

For gel filtration, polyvinyl gel TOYOPEARL HW40F (trademark) manufactured by Toyo Soda Mfg. Co., Ltd. was used.

EXAMPLE 1

Synthesis of H-PyroClu-Ala-Arg-CHA.HCl

I. BOC-Arg(NO$_2$)-CHA

After 50 3 g (0.158 mole) of BOC-Arg(NO$_2$)-OH was dissolved in 160 ml of DMF, 20.5 ml (0.158 mole) of NEM was added to the solution. Then, 21.2 ml (0.158 mole) of isobutyl chloroformate was dropwise added to the mixture at $-20°$ C. The resulting mixture was reacted for 10 minutes. After completion of the reaction, 250 ml of a solution of 30.0 g (0.158 mole) of 5-aminosalicylic acid hydrochloride and 61.6 ml (0.474 mole) of NEM in DMF was dropwise added to the reaction solution at $-15°$ to $-10°$ C. After the dropwise addition, the mixture was reacted at the same temperature for 3 hours and further at room temperature ($15°$ to $20°$ C.) for 18 hours. After the reaction, DMF was removed by distillation under reduced pressure and the residue was dissolved in 950 ml of AcOEt. After washing 4 times with 300 ml of cold 5% hydrochloric acid and twice with 300 ml of saturated sodium chloride aqueous solution, the solution was dried over anhydrous magnesium sulfate and decolored with activated charcoal. After drying, magnesium sulfate and activated charcoal were filtered off and the filtrate was cooled and settled. The precipitated crystals were taken by filtration and dried to give 46.2 g (46.3%) of Boc-Arg(NO$_2$)-CHA.

$R_{f1}=0.11$, m.p. 208° C. (decomposed)
$[\alpha]_D^{20}=-8.4$ (C=1, MeOH)

| Elemental analysis for $C_{18}H_{26}N_6O_8 \cdot \frac{1}{4}H_2O$ | | | |
|---|---|---|---|
| | C (%) | H (%) | N (%) |
| Found | 47.16 | 5.75 | 18.30 |
| Calcd. | 47.11 | 5.82 | 18.31 |

II. BOC-Ala-Arg(NO$_2$)-CHA

BOC-Arg(NO$_2$)-CHA, 45.4 g (0.1 mole), was dissolved in 300 ml (0.6 mole) of 2N HCl/AcOH and a small amount of MeOH. The solution was reacted at room temperature for 2 hours. After completion of the reaction, 300 ml of dry ether was added to the reaction mixture to crystallize, whereby 34.9 g (89.4%) of HCl.H-Arg(NO$_2$)-CHA was obtained.

$R_{f3}=0.31$, m.p. 193°-206° C.
$[\alpha]_D^{20}=+37.4$ (C=1, MeOH)

After 15.9 g (0.084 mole) of BOC-Ala-OH was dissolved in 84 ml of DMF, 10.9 ml (0.084 mole) of NEM was added to the solution. Then, 10.9 ml (0.084 mole) of isobutyl chloroformate was dropwise added to the solution at $-20°$ C. The resulting mixture was reacted for 10 minutes. After completion of the reaction, 84 ml of a solution of 32.8 g (0.084 mole) of HCl.H-Arg(NO$_2$)-CHA and 32.8 ml (0.252 mole) of NEM in DMF was dropwise added to the reaction solution at $-15°$ to $-10°$ C. After the dropwise addition, the mixture was reacted at the same temperature for 23 hours and further at room temperature ($15°$ to $20°$ C.) for 18 hours. After the reaction, DMF was removed by distillation under reduced pressure and the residue was dissolved in 600 ml of AcOEt. After washing 3 times with 200 ml of cold 5% hydrochloric acid and twice with 200 ml of saturated sodium chloride aqueous solution, the solution was dried over anhydrous magnesium sulfate and decolored with activated charcoal. After drying, magnesium sulfate and activated charcoal were filtered off and the solvent was removed by distillation under reduced pressure. Recrystallization of the residue gave 31.0 g (70.3%) of BOC-Ala-Arg(NO$_2$)-CHA.

$R_{f1}=0.12$, m.p 201°-212° C.
$[\alpha]_D^{20}=-16.0°$ (C=0.5, DMF)

| Elemental analysis for $C_{21}H_{31}N_7O_9 \cdot \frac{1}{4}H_2O$ | | | |
|---|---|---|---|
| | C (%) | H (%) | N (%) |
| Found | 47.25 | 6.25 | 18.55 |
| Calcd. | 47.19 | 6.03 | 18.34 |

III. Z-PyroGlu-Ala-Arg(NO₂)-CHA

BOC-Ala-Arg(NO$_2$)-CHA, 30.0 g (0.057 mole), was dissolved in 142.5 ml (0.285 mole) of 2N HCl/AcOH and a small amount of MeOH. The solution was reacted at room temperature for 2 hours. After completion of the reaction, 1000 ml of dry ether was added to the reaction mixture. The precipitated crystals were taken by filtration and dried to give 25.0 g (95.0%) of HCl.H-Ala-Arg(NO$_2$)-CHA.
$R_{f2}=0.13$, m.p. 178°–205° C.
$[\alpha]_D^{20} = -9.0°$ (C=0.5, DMF)

After 2.31 g (5.0 mmols) of HCl.H-Ala-Arg(NO$_2$)-CHA was dissolved in 10 ml (15.0 mmols) of 1.5N NEM/DMF, 1.93 g (5.0 mmols) of Z-PyroGlu-SDP was added to the solution at 0° to 5° C. The resulting mixture was reacted at room temperature for 18 hours. After completion of the reaction, the reaction solution was diluted with 300 ml of AcOH followed by washing 4 times with 100 ml of cold 5% hydrochloric acid and twice with 100 ml of saturated sodium chloride aqueous solution. After drying over anhydrous magnesium sulfate and decoloring with activated charcoal, the AcOEt phase was distilled under reduced pressure. The residue was recrystallized from MeOH/AcOEt/ether to give 18.4 g (54.9%) of Z-pyroGlu-Ala-Arg(NO$_2$)-CHA.
$R_{f2}=0.71$, m.p. 237° C. (decomposed)
$[\alpha]_D^{20} = -30.0°$ (C=0.5, DMF)

| Elemental analysis for C$_{28}$H$_{32}$N$_8$O$_{11}$.H$_2$O | | | |
|---|---|---|---|
| | C (%) | H (%) | N (%) |
| Found | 52.05 | 5.50 | 16.63 |
| Calcd. | 51.94 | 5.41 | 16.71 |

IV. H-PyroGlu-Ala-Arg-CHA.HCl

After 1.75 g (2.6 mmols) of Z-PyroGlu-Ala-Arg(NO$_2$)-CHA was suspended in a solvent mixture of 112.5 ml of MeOH, 27.7 ml of H$_2$O and 9.8 ml of 1N-HCl, 1 g of palladium black was added to the suspension followed by catalytic reduction at 30° C. for 6 hours. After the reaction, the catalyst was filtered off and the solvent was removed by distillation under reduced pressure. The residue was purified through TOYOPEARL HW40F column using MeOH as a developing solvent to give 0.471 g (34.4%) of H-PyroGlu-Ala-Arg-CHA.HCl.
$R_{f4}=0.25$
$[\alpha]_D^{20} = -63.0°$ (C=0.46, 1NHCL)

| Elemental analysis for C$_{21}$H$_{29}$N$_7$O$_7$HCl.½H$_2$O | | | |
|---|---|---|---|
| | C (%) | H (%) | N (%) |
| Found | 46.99 | 5.86 | 18.10 |
| Calcd. | 46.97 | 5.82 | 18.25 |

EXAMPLE 2

Synthesis of H-PyroGlu-Pro-Arg-CHA.HCl

I. BOC-Pro-Arg(NO₂)-CHA

After 39.1 g (0.1M) of H-Arg(NO$_2$)-CHA.HCl was dissolved in 200 ml of DMF, 42.0 ml (0.3M) of NEM was added to the solution Then, 33.7 ml (0.1 M) of BOC-Pro-SDP was added to the solution at 0° to 5° C. The resulting mixture was reacted at room temperature for 18 hours. After completion of the reaction, DMF was removed by distillation under reduced pressure and the residue was dissolved in 1000 ml of AcOEt. After washing with 300 ml of cold 5% hydrochloric acid and twice with 300 ml of saturated sodium chloride aqueous solution, the solution was dried over anhydrous magnesium sulfate and decolored with activated charcoal. After drying, magnesium sulfate and activated charcoal were filtered off and the solvent was removed by distillation under reduced pressure and the residue was recrystallized from MeOH/AcOEt/ether to give 27.7 g (50.3%) of Boc-Pro-Arg(NO$_2$)-CHA.
$R_{f1}=0.16$, m.p. 116° C. (decomposed)
$[\alpha]_D^{20} = -26°$ (C=0.5, DMF)

| Elemental analysis for C$_{23}$H$_{33}$N$_7$O$_9$.H$_2$O | | | |
|---|---|---|---|
| | C (%) | H (%) | N (%) |
| Found | 48.25 | 6.45 | 17.55 |
| Calcd. | 48.50 | 6.19 | 17.21 |

II. Z-PyroGlu-Pro-Arc(NO₂)-CHA

BOC-Pro-Arg(NO$_2$)-CHA, 26.0 g (0.047 mole), was dissolved in 117.5 ml (0.235 mole) of 2N Hcl/AcOH and a small amount of MeOH. The solution was reacted at room temperature for 2 hours. After completion of the reaction, 900 ml of dry ether was added to the reaction mixture. The precipitated crystals were taken by filtration and dried to give 19.8 g (93.3%) of HCl.H-Pro-Arg(NO$_2$)-CHA.
$R_{f2}=0.08$, m.p. 88–°93° C.
$[\alpha]_D^{20} = -35.8°$ (C=1, MeOH)

After 2.25 g (5.0 mmols) of HCl.H-Pro-Arg(NO$_2$)-CHA was dissolved in 10 ml (15.0 mmols) of 1.5N NEM/DMF, 1.93 g (5.0 mmols) of Z-PyroGlu-SDP was added to the solution at 0° to 5° C. The resulting mixture was reacted at room temperature for 18 hours. After completion of the reaction, the reaction solution was diluted with 300 ml of AcOH followed by washing 4 times with 100 ml of cold 5% hydrochloric acid and twice with 100 ml of saturated sodium chloride aqueous solution. After drying over anhydrous magnesium sulfate and decoloring with activated charcoal, the AcOEt phase was distilled under reduced pressure. The residue was recrystallized from MeOH/AcOEt/ether to give 1.86 g (53.4%) of Z-PyroGlu-Pro-Arg(NO$_2$)-CHA.
$R_{f2}=0.69$, m.p. 220° C. (decomposed)
$[\alpha]_D^{20} = -18°$ (C=0.5, DMF)

| Elemental analysis for C$_{31}$H$_{36}$N$_8$O$_{11}$.H$_2$O | | | |
|---|---|---|---|
| | C (%) | H (%) | N (%) |
| Found | 52.13 | 5.40 | 15.75 |
| Calcd. | 52.10 | 5.36 | 15.68 |

III. H-PyroGlu-Pro-Arg-CHA.HCl

After 0.60 g (0.87 mmol) of Z-PyroGlu-Pro-Arg(NO$_2$)-CHA was suspended in a solvent mixture of 112.5 ml of MeOH, 35.8 ml of H$_2$O and 1.7 ml of 1N-HCl, 1 g of palladium black was added to the suspension followed by catalytic reduction at 30° C. for 5 hours. After the reaction, the catalyst was filtered off and the solvent was removed by distillation under reduced pressure. The residue was purified through TOYOPEARL HW40F column using MeOH as a developing solvent to give 0.42 g (87.5%) of H-PyroGlu-Pro-Arg-CHA.HCl
$R_{f3}=0.26$, m.p. 155° C. (decomposed)

$[\alpha]_D^{20} = -92°$ (C=0.5, MeOH)

Elemental analysis for $C_{23}H_{31}N_7O_7.H_2O$

|  | C (%) | H (%) | N (%) |
|---|---|---|---|
| Found | 48.33 | 5.70 | 17.30 |
| Calcd. | 48.29 | 5.99 | 17.14 |

EXAMPLE 3

Synthesis of H-D-Glu(O'Bu)-Gly-Arg-CHA.2HCl

I. BOC-Arg-CHA.HCl

After 381.1 g (1.16 mole) of BOC-Arg-OH.HCl.H$_2$O was dissolved in 1392 ml of DMF, 151 ml of NEM was added to the solution. Then, 152.3 ml of isobutyl chloroformate was dropwise added to the solution at −20° C. The resulting mixture was reacted for 10 minutes. After the reaction, 928 ml of a solution of 219.8 g (1.16 mole) of 5-aminosalicylic acid hydrochloride and 301.6 ml of NEM in DMF was dropwise added to the reaction solution at −15° to −10° C. After the dropwise addition, the mixture was reacted at the same temperature for 3 hours and further at room temperature for 15 hours. After the reaction, DMF was removed by distillation under reduced pressure and the residue was dissolved in 464 ml of MeOH and 332 ml of n-BuOH. To the solution was added 3300 ml of AcOEt. After washing twice with 2160 ml of cold 5% hydrochloric acid saturated with sodium chloride, the mixture was dried over anhydrous magnesium sulfate. After drying, magnesium sulfate was filtered off and the solvent was removed by distillation under reduced pressure to give 464.8 g (89.9%) of Boc-Arg-CHA.HCl.

$R_{f2} = 0.64$, m.p. 225.0° C. (decomposed)
$[\alpha]_D^{20} = -10.7°$ (C=1, MeOH)

Elemental analysis for $C_{18}H_{28}N_5O_6Cl.H_2O$

|  | C (%) | H (%) | N (%) |
|---|---|---|---|
| Found | 46.71 | 6.60 | 14.90 |
| Calcd. | 46.60 | 6.52 | 15.10 |

II. BOC-Gly-Arg-CHA.HCl

BOC-Arg-CHA.HCl, 243.7 g (0.55 mole), was dissolved in 1093 ml of 2N HCl/AcOH and a small amount of MeOH. The solution was reacted at room temperature for an hour. After completion of the reaction, 1093 ml of isopropanol was added to the reaction mixture to cause precipitation again in AcOEt. The precipitated crystals were taken by filtration and dried to give 156.2 g (74.3%) of H-Arg-CHA.2HCl.

$R_{f4} = 0.15$, m.p. 240.5° C. (decomposed)
$[\alpha]_D^{20} = +53.5°$ (C=1, H$_2$O)

After 109.2 g (0.27 mol) of H-Arg-CHA.2HCl was dissolved in 290 ml of DMF, 70.2 ml (0.54 mol) of NEM was added to the solution. Further 81.7 g (0.3 mol) of BOC-Gly-OSu was added thereto at 0° to 5° C. The resulting mixture was reacted at room temperature for 18 hours. After completion of the reaction, DMF was distilled under reduced pressure. The residue was dissolved in 500 ml of MeOH and the solution was reprecipitated in 8 liters of AcOEt. The precipitated crystals were taken by filtration and dried to give 135.8 g (100%) of BOC-Gly-Arg-CHA.HCl.

$R_{f2} = 0.46$, m.p. 214.5° C. (decomposed)
$[\alpha]_D^{20} = -22°$ (C=1, MeOH)

Elemental analysis for $C_{20}H_{30}N_6O_7.HCl.H_2O$

|  | C (%) | H (%) | N (%) |
|---|---|---|---|
| Found | 46.55 | 6.80 | 16.15 |
| Calcd. | 46.11 | 6.39 | 16.13 |

III. Z-D-Glu(O'Bu)-Gly-Arg-CHA.HCl

After 125.7 g (0.25 mol) of BOC-Gly-Arg-CHA.HCl was dissolved in a small amount of MeOH, 500 ml (0.10 mol) of 2N HCl/AcOH was added to the solution. The mixture was reacted at room temperature for an hour with stirring. After completion of the reaction, the reaction mixture was reprecipitated in 4.5 liters of ether. The precipitated crystals were taken by filtration and dried to give 109.8 g (100%) of H-Gly-Arg-CHA.2HCl.

$R_{f3} = 0.09$, m.p. 219.5° C. (decomposed)
$[\alpha]_D^{20} = -21.0°$ (C=1, AcOH:H$_2$O=1:1))

After 4.4 g (10 mM) of H-Gly-Arg-CHA.2HCl was dissolved in 20 ml of 0.75N NEM/DMF, 4.3 g (10 mM) of Z-D-Glu(O'Bu)-OSu was added to the solution while cooling to 0° to 5° C. with stirring. The resulting mixture was reacted at room temperature for 15 hours. After completion of the reaction, the solvent was distilled under reduced pressure. The residue was dissolved in MeOH and the solution was reprecipitated in 1 liter of AcOEt. The precipitated crystals were taken by filtration and dried to give 6.1 g (84.5%) of Z-D-Glu(O'Bu)-Gly-Arg-CHA.HCl.

$R_{f2} = 0.60$, m.p. 195.0° C. (decomposed)
$[\alpha]_D^{20} = -7.0°$ (C=0.5, MeOH)

Elemental analysis for $C_{32}H_{43}N_7O_{10}$ HCl.1.5H$_2$O

|  | C (%) | H (%) | N (%) |
|---|---|---|---|
| Found | 51.45 | 6.10 | 13.10 |
| Calcd. | 51.30 | 6.19 | 13.09 |

II. H-D-Glu(O'Bu)-Gly-Arg-CHA.2HCl

After 5.5 g (7.6 mM) of Z-D-Glu(O'Bu)-Gly-Arg-CHA was dissolved in 150 ml of MeOH, 1 g of palladium black was added to the solution followed by catalytic reduction at 30° C. for 5 hours. After the reaction, the catalyst was filtered off and the solvent was removed by distillation under reduced pressure. The residue was dissolved in 5.5 ml of 5% HCl-MeOH and 20 ml of MeOH. The solution was precipitated again in ether. The precipitates were taken out by filtration and dried and then purified through TOYOPEARL HW40F column using MeOH as a developing solvent to give 3.6 g (75.8%) of H-D-Glu(O'Bu)-Gly-Arg-CHA.2HCl.

$R_{f3} = 0.35$, m.p. 168.5° C. (decomposed)
$[\alpha]_D^{20} = -3.0°$ (C=0.5, MeOH)

Elemental analysis for $C_{24}H_{37}N_7O_8.2HCl.\frac{1}{2}H_2O$

|  | C (%) | H (%) | N (%) |
|---|---|---|---|
| Found | 45.48 | 6.43 | 15.35 |
| Calcd. | 45.50 | 6.36 | 15.48 |

EXAMPLE 4

Substrates shown in Table 2 were synthesized in a manner similar to Example 1, 2 or 3. Physical properties of the substrates are also shown in Table 2.

TABLE 2

| Substrate | m.p. (°C.) | $R_\beta$ | $[\alpha]_D^{20}$ (C = 0.5) |
|---|---|---|---|
| PS-1290 H—D—PyroGlu—Ala—Arg—CHA.HCl | 173–178 | 0.40 | −44.5° (H$_2$O) |
| PS-1291 H—D—PyroGlu—Pro—Arg—CHA.HCl | 180 (decomp.) | 0.35 | −89.0° (50% AcOH) |
| PS-1292 H—PyroGlu—Pip—Arg—CHA.HCl | 188 (decomp.) | 0.35 | −93.0° (50% AcOH) |
| PS-1293 H—PyroGlu—Val—Arg—CHA.HCl | 191–205 | 0.48 | −58.5° (50% AcOH) |
| PS-1294 H—PyroGlu—But—Arg—CHA.HCl | 184–192 | 0.43 | −65.0° (H$_2$O) |
| PS-1295 H—PyroGlu—NVal—Arg—CHA.HCl | 167–175 | 0.48 | −55.2° (50% AcOH) |
| PS-1296 H—PyroGlu—NLeu—Arg—CHA.HCl | 191–198 | 0.49 | −54.6° (50% AcOH) |
| PS-1297 H—D—Glu(OCH$_3$)—Gly—Arg—CHA.2HCl | 170 (decomp.) | 0.33 | −4.0° (MeOH) |
| PS-1298 H—D—Glu—Gly—Arg—CHA.2HCl | 190 (decomp.) | 0.25 | −60.0° (H$_2$O) |
| PS-1299 H—D—Glu(O$^n$Pr)—Gly—Arg—CHA.2HCl | 185 (decomp.) | 0.35 | −55.0° (H$_2$O) |
| Ps-1300 H—D—Glu(O$^i$Pr)—Gly—Arg—CHA.2HCl | 180 (decomp.) | 0.37 | −56.0° (H$_2$O) |

Results on elemental analyses of the substrates of the present invention shown in Table 2 are presented in Table 3.

TABLE 3

| | Found (%) | Calcd (%) |
|---|---|---|
| PS-1290 | H—D—PyroGlu—Ala—Arg—CHA.HCl | Calcd. for C$_{21}$H$_{29}$N$_7$O$_7$.HCl.½H$_2$O |
| C | 46.80 | 46.97 |
| H | 5.70 | 5.82 |
| N | 18.40 | 18.26 |
| PS-1291 | H—D—PyroGlu—Pro—Arg—CHA.HCl | Calcd. for C$_{23}$H$_{31}$N$_7$O$_7$.HCl.H$_2$O |
| C | 48.25 | 48.29 |
| H | 5.90 | 5.99 |
| N | 17.30 | 17.14 |
| PS-1292 | H—PyroGlu—Pip—Arg—CHA.HCl | Calcd. for C$_{24}$H$_{33}$N$_7$O$_7$.HCl.H$_2$O |
| C | 49.20 | 49.19 |
| H | 6.30 | 6.19 |
| N | 16.65 | 16.73 |
| PS-1293 | H—PyroGlu—Val—Arg—CHA.HCl | Calcd. for C$_{23}$H$_{33}$N$_7$O$_7$.HCl.½H$_2$O |
| C | 49.20 | 49.15 |
| H | 6.35 | 6.22 |
| N | 17.20 | 17.45 |
| PS-1294 | H—PyroGlu—But—Arg—CHA.HCl | Calcd. for C$_{22}$H$_{3k}$N$_7$O$_7$.HCl.H$_2$O |
| C | 47.05 | 47.19 |
| H | 6.30 | 6.12 |
| N | 17.35 | 17.51 |
| PS-1295 | H—PyroGlu—NVal—Arg—CHA.HCl | Calcd. for C$_{23}$H$_{33}$N$_7$O$_7$.HCl.½H$_2$O |
| C | 49.18 | 49.15 |
| H | 6.40 | 6.22 |
| N | 17.60 | 17.45 |
| PS-1296 | H—PyroGlu—NLeu—Arg—CHA.HCl | Calcd. for C$_{24}$H$_{35}$N$_7$O$_7$.HCl.½H$_2$O |
| C | 49.90 | 50.17 |
| H | 6.50 | 6.40 |
| N | 17.05 | 17.06 |
| PS-1297 | H—D—Glu(OCH$_3$)—Gly—Arg—CHA.HCl | Calcd. for C$_{21}$H$_{31}$N$_7$O$_8$.2HCl.H$_2$O |
| C | 42.20 | 42.01 |
| H | 6.00 | 5.88 |
| N | 16.55 | 16.33 |
| PS-1298 | H—D—Glu—Gly—Arg—CHA.2HCl | Calcd. for C$_{20}$H$_{31}$N$_7$O$_8$Cl$_2$.2H$_2$O |
| C | 39.77 | 39.74 |
| H | 5.68 | 5.84 |
| N | 15.92 | 16.22 |
| PS-1299 | H—D—Glu(O$^n$Pr)—Gly—Arg—CHA.2HCl | Calcd. for C$_{23}$H$_{37}$N$_7$O$_8$Cl$_2$.2H$_2$O |
| C | 42.48 | 42.73 |
| H | 6.26 | 6.39 |
| N | 14.87 | 15.17 |
| PS-1300 | H—D—Glu(O$^i$Pr)—Gly—Arg—CHA.2HCl | Calcd. for C$_{23}$H$_{37}$N$_7$O$_8$Cl$_2$.2H$_2$O |
| C | 42.74 | 42.73 |
| H | 6.19 | 6.39 |
| N | 15.17 | 15.17 |

EXAMPLE 5

Specificity of each of the new substrates synthesized in Examples 1 through 4 was examined by reacting with each enzyme. Details of reagents used are as described below.
(1) Substrate: 10 mmol/l
(2) Buffer: concentration of Tris, NaCl and CaCl₂ and The measurement results are shown in Table 4.

As is evident from Table 4, the substrates of the present invention shown high specificity to trypsin, as compared to known substrate.

TABLE 4

| Comparison in Substrate | | | | | |
|---|---|---|---|---|---|
| | Substrate | | | | |
| Substrate for control | Try | TH | PL | KL | FXa |
| CHR—Try Z—Val—Gly—Arg—PNA | 0.243 | 0.050 | 0.014 | 0.008 | 0.090 |
| Substrate of the present invention | | | | | |
| PS-1242 H—PyroGlu—Pro—Arg—CHA | 0.570 | 0.022 | 0.013 | 0.004 | 0.008 |
| PS-1245 H—PyroGlu—Ala—Arg—CHA | 0.676 | 0.006 | 0.005 | 0.005 | 0.008 |
| PS-1290 H—D—PyroGlu—Ala—Arg—CHA | 0.403 | 0.005 | 0.000 | 0.002 | 0.007 |
| PS-1291 H—D—PyroGlu—Pro—Arg—CHA | 0.556 | 0.012 | 0.004 | 0.002 | 0.007 |
| PS-1292 H—PyroGlu—Pip—Arg—CHA | 0.814 | 0.021 | 0.005 | 0.002 | 0.007 |
| PS-1293 H—PyroGlu—Val—Arg—CHA | 0.434 | 0.002 | 0.007 | 0.002 | 0.007 |
| PS-1294 H—PyroGlu—But—Arg—CHA | 0.588 | 0.003 | 0.008 | 0.003 | 0.010 |
| PS-1295 H—PyroGlu—NVal—Arg—CHA | 0.637 | 0.002 | 0.008 | 0.006 | 0.008 |
| PS-1296 H—PyroGlu—NLeu—Arg—CHA | 0.656 | 0.002 | 0.010 | 0.006 | 0.008 |
| PS-1297 H—D—Glu(OCH₃)—Gly—Arg—CHA | 0.585 | 0.002 | 0.005 | 0.002 | 0.005 |
| PS-1298 H—D—Glu—Gly—Arg—CHA | 0.401 | 0.002 | 0.004 | 0.003 | 0.004 |
| PS-1299 H—D—Glu(OⁿPr)—Gly—Arg—CHA | 0.503 | 0.005 | 0.005 | 0.006 | 0.020 |
| PS-1300 H—D—Glu(OⁱPr)—Gly—Arg—CHA | 0.595 | 0.003 | 0.006 | 0.004 | 0.021 |
| PS-1301 H—D—Glu(OᵗBu)—Gly—Arg—CHA | 0.538 | 0.007 | 0.002 | 0.003 | 0.023 |

Initial substrate concentration: So = 0.4 mmol
Numerals indicate absorbance (O.D.) measured.
Wavelengths measured were at 405 nm with respect to CHR—TRY and at 700 nm with respect to PS-1242, PS-1245 and PS-1290 through 1301.

pH (25° C.) were set as shown below, depending upon enzyme.

| | Trypsin (Try) | Thrombin (TH) | Plasmin (PL) | Normal | |
|---|---|---|---|---|---|
| | | | | Factor Xa (FXa) | Kallikrein (KL) |
| Tris (mmol) | 100 | 50 | 50 | 50 | 50 |
| NaCl (mmol) | 150 | 150 | 150 | 250 | 150 |
| CaCl₂ (mmol) | 0 | 0 | 0 | 50 | 0 |
| pH (25° C.) | 8.0 | 8.5 | 7.8 | 8.3 | 7.8 |

(3) Enzyme used:
Enzyme used and its source, etc. are as follows.

| | Source | Manufacture | Lot | Unit |
|---|---|---|---|---|
| Trypsin | Bovine | Wersinton | 31M771 | 10 μg/ml |
| Thrombin | Bovine | Mochida Pharmaceutical Company | 65146 | 4.0 NIH/ml |
| Plasmin | Human | Green Cross Company | PL-35 | 0.25 CU/ml |
| Kallikrein | Swine | Sigma Inc. | 32F-0810 | 1.0 U/ml |
| Factor X | Bovine | Sigma Inc. | 73F-9450 | 0.4 U/ml |

(4) Terminate solution (PNA): 10% acetic acid
(5) Color forming reagent (CHA): pentacyanoamineferroate Method Buffer, 0.5 ml and 0.1 ml of substrate solution are charged in a silicone-treated hard glass test tube or plastic test tube. The mixture is previously heated for 10 minutes in a thermostat at 37° C. Then, 0.1 ml of enzyme solution is added to the mixture to perform enzyme reaction at 37° C. for 5 minutes. Accurately 5 minutes after, 2.0 ml of the terminate solution is added to stop the enzyme reaction. Then the reaction mixture is allowed to stand at 37° C. for 10 minutes and its absorbance is measured at 405 nm or 700 nm.

While the invention has been described in detail and with reference to specific embodiments thereof, it will be apparent to one skilled in the art that various changes and modifications can be made therein without departing from the spirit and scope thereof.

What is claimed is:

1. A substrate for determination of enzyme activity represented by the following formula:

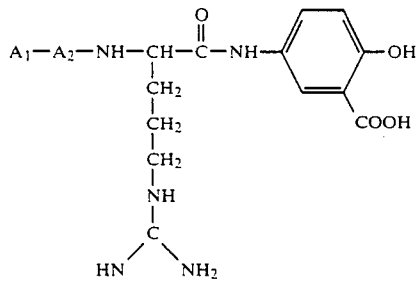

wherein
A₁ represents L- or D-PyroGlu or L- or D-Glu(OR), wherein OR is a group binding to γ-carboxyl group of glutamic acid; R represents hydrogen or an aliphatic hydrocarbon residue of 1 to 8 carbon atoms or a cycloalkyl having from 3 to 8 carbon atoms; and,
A₂ represents Gly, Pro, Pip, Ala, Val, But, NVal or NLeu; and acid addition salts thereof.

2. The substrate as claimed in claim 1, wherein said substrate is used for the determination of trypsin activity.

3. A substrate as claimed in claim 1, wherein A₁ is L- or D-Glu(OR) and R is an alkyl group of 1 to 8 carbon atoms or a cycloalkyl group of 3 to 8 carbon atoms.

4. A substrate as claimed in claim 1, wherein R is an alkyl group of 1 to 4 carbon atoms.

5. A substrate as claimed in claim 1, wherein said addition salt is a hydrochloride.

* * * * *